United States Patent
Wendland et al.

(10) Patent No.: US 11,631,487 B2
(45) Date of Patent: Apr. 18, 2023

(54) SYSTEM AND METHOD FOR SUPPORTING ON THE USE OF AN INJECTION DEVICE

(71) Applicant: SANOFI, Paris (FR)

(72) Inventors: Stefan Wendland, Frankfurt am Main (DE); Michael Harms, Frankfurt am Main (DE); Zdenek Cerman, Frankfurt am Main (DE)

(73) Assignee: Sanofi, Paris (FR)

(*) Notice: Subject to any disclaimer, the term of this patent is extended or adjusted under 35 U.S.C. 154(b) by 26 days.

(21) Appl. No.: 16/763,289

(22) PCT Filed: Nov. 15, 2018

(86) PCT No.: PCT/EP2018/081302
§ 371 (c)(1),
(2) Date: May 12, 2020

(87) PCT Pub. No.: WO2019/096875
PCT Pub. Date: May 23, 2019

(65) Prior Publication Data
US 2020/0312437 A1  Oct. 1, 2020

(30) Foreign Application Priority Data
Nov. 15, 2017 (EP) .................................... 17306586

(51) Int. Cl.
*G16H 20/17* (2018.01)
*G16H 40/63* (2018.01)

(52) U.S. Cl.
CPC ............. *G16H 20/17* (2018.01); *G16H 40/63* (2018.01); *A61M 2205/505* (2013.01); *A61M 2205/52* (2013.01)

(58) Field of Classification Search
CPC ........ G16H 20/10; G16H 40/20; G16H 20/17; G16H 20/40
See application file for complete search history.

(56) References Cited

U.S. PATENT DOCUMENTS

| | | | | |
|---|---|---|---|---|
| 2009/0317002 A1* | 12/2009 | Dein | ...................... | A61B 90/90 340/568.1 |
| 2015/0209510 A1* | 7/2015 | Burkholz | ................ | G06F 3/011 604/93.01 |
| 2017/0252108 A1* | 9/2017 | Rios | ........................ | G16H 40/63 |

FOREIGN PATENT DOCUMENTS

| | | | | |
|---|---|---|---|---|
| CA | 2517045 A1 * | 2/2006 | ............... | B07C 3/14 |
| EP | 3200109 | 8/2017 | | |

(Continued)

OTHER PUBLICATIONS

Bouget, David, et al. "Vision-based and marker-less surgical tool detection and tracking: a review of the literature." Medical image analysis 35 (2017): 633-654. (Year: 2017).*

(Continued)

*Primary Examiner* — Linh Giang Le
*Assistant Examiner* — Constantine Siozopoulos
(74) *Attorney, Agent, or Firm* — Fish & Richardson P.C.

(57) ABSTRACT

A system for supporting on the use of an injection device includes a display and a processor configured to determine the injection device, to obtain data on use of the determined injection device and to add at least one overlay on the display, wherein the at least one overlay is generated depending on the obtained data on use of the determined injection device. The processor is configured to adapt the at least one overlay depending on a context of application of the injection device, the context of application of the injection device including at least one of the following: ambient light; time; date; temperature; use history of the injection device; drug; injection site; dosage.

20 Claims, 3 Drawing Sheets

(56) References Cited

FOREIGN PATENT DOCUMENTS

| | | |
|---|---|---|
| JP | 2017-513086 | 5/2017 |
| JP | 2017-524427 | 8/2017 |
| JP | 2018-007226 | 1/2018 |

OTHER PUBLICATIONS

PCT International Preliminary Report on Patentability in Application No. PCT/EP2018/081302, dated May 19, 2020, 6 pages.
PCT International Search Report and Written Opinion in Application No. PCT/EP2018/081302, dated Feb. 18, 2019, 8 pages.
Uranishi et al., "Blood Collection Trainer with Visualization of Failure," The Virtual Reality Society of Japan, Jul. 4, 2017, 22(2):217-227 (with English abstract).

* cited by examiner

SYSTEM AND METHOD FOR SUPPORTING ON THE USE OF AN INJECTION DEVICE

CROSS-REFERENCE TO RELATED APPLICATIONS

The present application is the national stage entry of International Patent Application No. PCT/EP2018/081302, filed on Nov. 15, 2018, and claims priority to Application No. EP 17306586.3, filed on Nov. 15, 2017, the disclosures of which are incorporated herein by reference.

TECHNICAL FIELD

This relates to a system and method for supporting on the use of an injection device.

BACKGROUND

Injection devices, such as auto-injectors, are known in the art for dispensing a medicament to the injection site of a patient. Injections by using injection devices can be applied either by medical personnel or by patients themselves. For application of an injection device, it may be helpful especially for patients to obtain support on the use of an injection device.

SUMMARY

A first aspect provides a system for supporting on the use of an injection device comprising a display and a processor being configured to determine the injection device, to obtain data on use of the determined injection device and to add at least one overlay on the display, wherein the at least one overlay is generated depending on the obtained data on use of the determined injection device. The system may for instance be implemented by a mobile computing device, particularly a handheld device, such as a smartphone or a tablet computer, or a wearable device, such as an optical head-mounted display. However, also a computer coupled to a camera or having a built-in camera, for instance a webcam, can be used instead. A display may be a transparent display, on which the at least one overlay is projected or displayed, such as utilized in an optical head-mounted display, a non-transparent display, on which the at least one overlay is displayed together with a representation of an image of the injection device captured with an image component, such as utilized in a smartphone, a tablet computer, a head-mounted display with active displays like LCD or OLED screens, or a virtual display such as the retina of a viewer's eye. The system may be used to implement an augmented reality support of patients and medical personnel on using the injection device.

The at least one overlay may comprise textual information, a video and/or one or more images. For instance, the textual information may comprise hints on the use of the injection device, the video may be a training video showing proper use of the injection device, and the images may show different aspects of the use of the injection devices.

The processor may be configured to determine the injection device with image processing of a captured image of the injection device, wherein the image processing comprises detecting a form of, a color of, a code, a tag and/or a label on the injector device, and determining the injection device depending on of the detected form, color, code, tag, label.

The processor may be configured to determine the injection device by receiving injection device identification data. For instance, the injection device identification data can be electronically stored in an internal storage of the injection device. The internal storage may be for instance implemented by a RFID or NFC chip or tag. The system may for instance comprise a wireless receiver for receiving the injection device identification data, wherein the wireless receiver particularly comprises at least one of the following: a RFID reader; a NFC reader; a Bluetooth® receiver.

The system may comprise an image capturing component to capture an image of the injection device, wherein the processor is configured to display the captured image of the injection device on the display together with the at least one overlay. For instance, a mobile computing device with a built-in camera such as a smartphone can be used to capture the image and display it on its own screen together with the overlay(s).

The processor may be configured to adapt the at least one overlay depending on environmental conditions, particularly depending on of the following: ambient light, time, date, temperature. For instance, an overlay may be displayed in different colors depending on time, date and/or temperature, such as in red color when it is too late for an injection or the ambient temperature is outside a predetermined temperature range for injection.

The processor may be configured to generate the at least one overlay by loading the data on use of the determined injection device from an internal storage and/or from an external storage by means of a data connection, particularly a wireless data connection. For instance, if the system is implemented by a mobile computing device having a data connection, the information can be downloaded from a webserver via a secured data connection. Alternatively, or additionally, some or all the information can also be stored in an internal storage of the system, for example in a non-volatile memory of a mobile computing device.

The processor may be configured to detect user actions and to adapt the at least one overlay depending on detected user actions. User actions may comprise for instance user inputs via buttons, or gestures, or voice commands. The user actions may be processed by the processor for instance to control the representation of the at least one overlay, for example by sequentially displaying various instructions and/or hints for the use of the injection device depending on processed user actions.

The processor may be configured to store data regarding a use history of the injection device. Use history data may for instance comprise time and date stamps of a usage of the injection device, injection site, and injection dose.

Another aspect of the specification provides a method for supporting on the use of an injection device comprising determining the injection device, obtaining data on use of the determined injection device and adding at least one overlay on a display, wherein the at least one overlay is generated depending on the obtained data on use of the determined injection device.

Another aspect of the specification provides a device comprising a processor, a memory, a display, a camera, and a software stored in a non-volatile part of the memory, wherein the software configures the processor of the device to capture one or more images of an injection device with the camera, to show a captured image of the injection device on the display, to determine the injection device, to obtain data on use of the determined injection device and to add at least one overlay on the display, wherein the at least one overlay is generated depending on the obtained data on use of the determined injection device.

The device may be for example a smartphone, a Personal Digital Assistant, a tablet or laptop computer, or a head-mounted display device.

The adapting of the at least one overlay depending on a context of application of the injection device may comprise at least one of the following: displaying the overlay in different colors depending on at least one of the following: ambient light; time; date; temperature; use history of the injection device; drug; injection site; dosage; altering the displayed content of the overlay depending on at least one of the following: ambient light; time; date; temperature; use history of the injection device; drug; injection site; dosage; altering the size of the overlay depending on at least one of the following: ambient light; time; date; temperature; use history of the injection device; drug; injection site; dosage; selecting the position of the overlay on the display depending on at least one of the following: ambient light; time; date; temperature; use history of the injection device; drug; injection site; dosage.

BRIEF DESCRIPTION OF THE FIGURES

In the Figures.

DETAILED DESCRIPTION

The system and method described herein can be advantageously used for training and assisting of a patient or a user of an injection device, particularly an auto-injector device, via augmented reality. The system and method utilizes an augmented reality application, for example embedded in a smartphone, to display one or more overlays on a display, such as a smartphone screen or lenses of an optical head-mounted display, with overlay(s) being generated by a processor depending on data on use of an injection device.

An overlay may comprise information such as training videos for the proper use of the injection device, a history of the usage of the injection device, safety information for a user, step-by-step guidance information for the proper use of the injection device, alerts, usage feedback, and the like. Thus, the system and method may provide support on the use of the injection device, particularly provide additional training and safety for the user.

A system according to embodiments can be implemented by a display for representing the overlay(s) and a processor configured to determine the injection device, for which support is required, to obtain data on use of the determined injection device, and to generate one or more overlays depending on the obtained data and a context of application of the injection device, which may comprise at least one of the following: ambient light; time; date; temperature; use history of the injection device; drug; injection site; dosage.

A smartphone or a head-mounted display with a software implementing an "augmented reality" system according to embodiments can be used as hardware. The hardware can be also configured to determine the injection device for which an augmented reality representation should be generated. The determination can be implemented by making a scan of the injection device or by receiving identification data of the injection device.

After determination of the injection device, data on use of the injection device can be loaded, for example a training video demonstrating proper use of the injection device, an instruction manual, and/or a usage history of the injection device.

Figure 1:
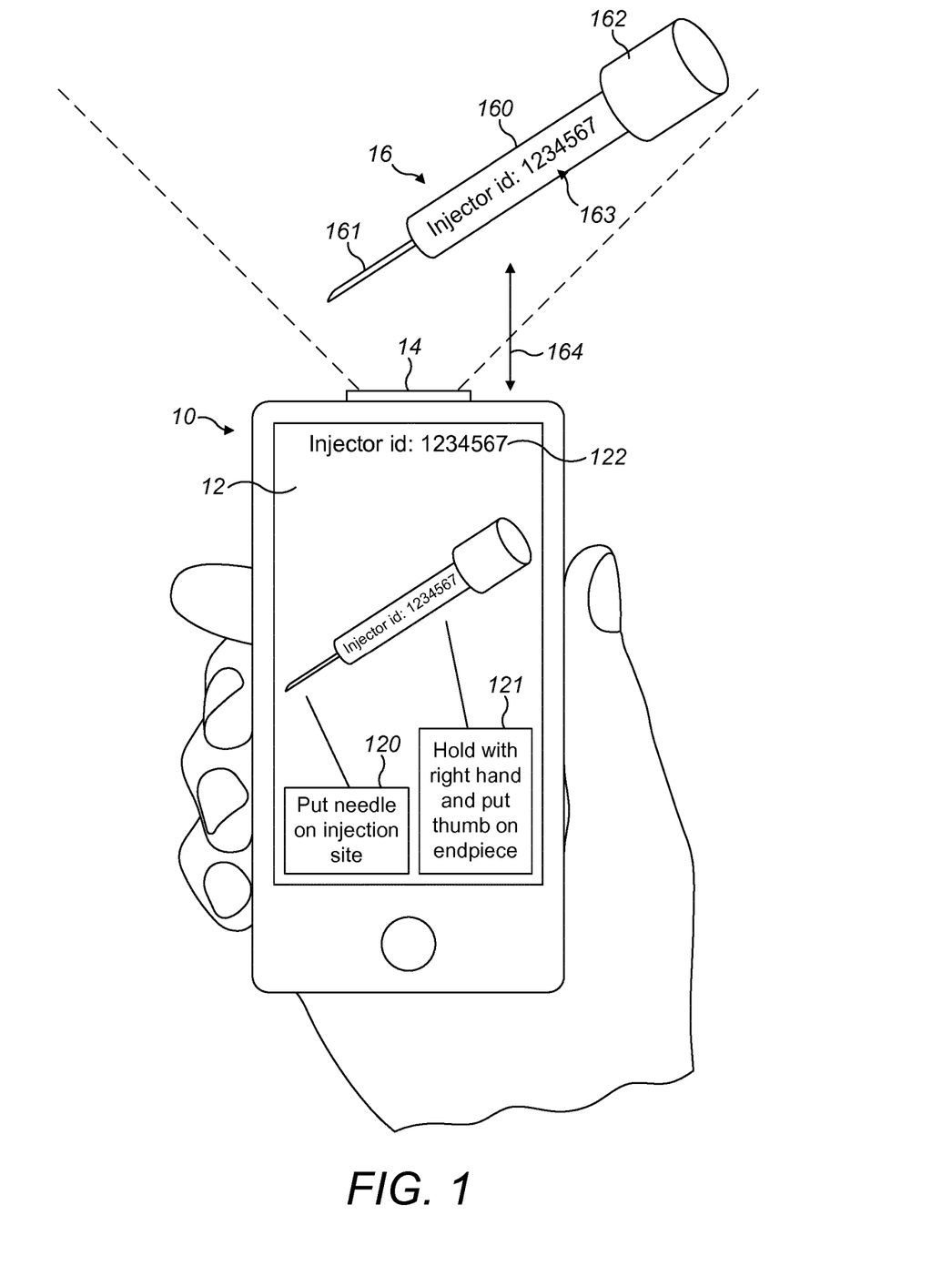
FIG. 1 shows a system according to embodiments.

FIG. 1 shows an implementation of the inventive system by means of a smartphone 10 comprising an LCD, TFT (thin film transistor), OLED (organic light emitting diode) or ePaper screen as display 12 and an integrated camera module as image capturing component 14. The smartphone 10 is configured by a software such as an "app" downloaded to and installed on the smartphone to implement the inventive system.

Figure 2:
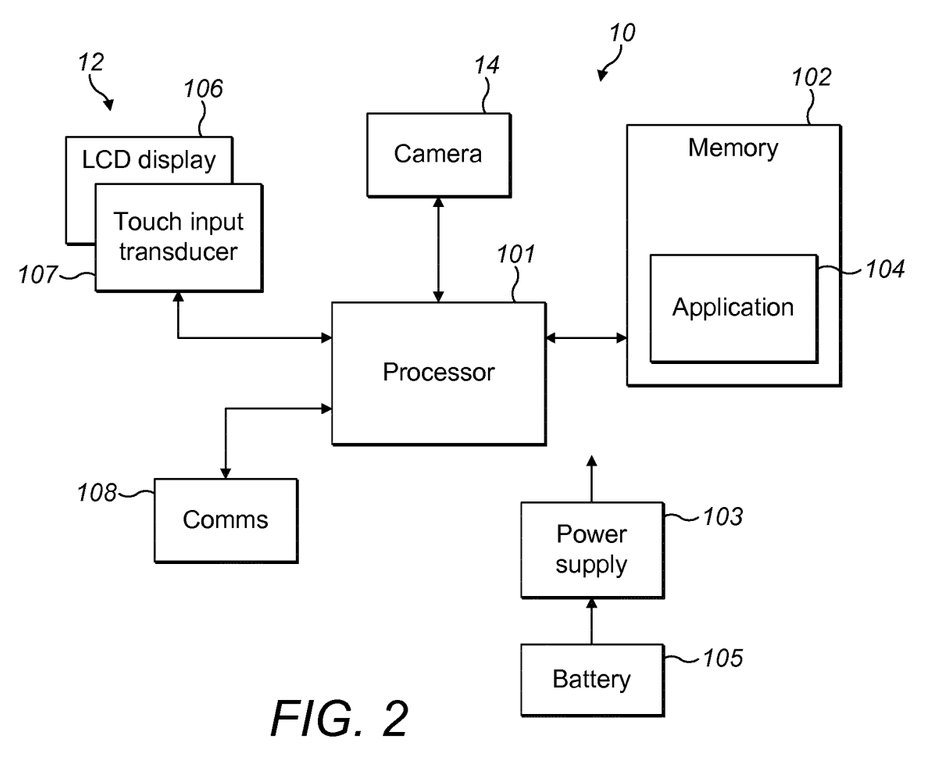
FIG. 2 shows a schematic view of a device of the system according to embodiments.

FIG. 2 is a schematic view of the smartphone 10 of FIG. 1 showing internal components of the smartphone 10. The smartphone 10 comprises a memory 102, i.e. a working or volatile memory, such as Random Access Memory (RAM), and a non-volatile memory. The non-volatile memory stores an operating system and the software 104 for supporting on the use of an injection device, which advantageously is a distinct application, as well as storing data files and associated metadata. The software 104 may be provided in the smartphone 10 on manufacture or it may be downloaded into the smartphone 10, for instance from an application market place or application store, or it may be side loaded into the smartphone 10. The display 12 of the smartphone 10 may be a touch sensitive display having a display part 106 and a tactile interface part 107. The smartphone 10 also includes a communications interface 108, such as a Bluetooth, a cellular radio and/or a WLAN (Wireless Local Area Network) interface. The smartphone 10 is further equipped with an ambient light sensor for detecting the ambient light at the location of the smartphone 10. Furthermore, the smartphone 10 may be equipped with a temperature sensor for measuring the ambient temperature, for example the room temperature. The smartphone 10 also houses a battery 105 to power the smartphone 10 by a power supply 103. The camera 14 of the smartphone 10 may be of a digital type and may comprise an imaging sensor for digitally capturing images, which can be stored in the RAM or the non-volatile memory. A processor 101 of the smartphone 10 is configured to send and receive signals to and from the other components in order to control operation of the other components. For example, the processor 101 controls the display of content on display 106 and receives signals as a result of user inputs from tactile interface 107. The display 106 may be a resistive touch screen or capacitive touch screen of any kind. The display may alternatively not be a touch screen. For instance, it may be a liquid crystal display (LCD).

The software 104 configures the processor 101 of the smartphone 10 to capture images of an injection device 16 with the camera module 14 and to display the captured images on the display 12 of the smartphone 10 so that the real injection device 16 is displayed on the display 12.

Thereafter, the software configures the processor to determine the injection device 16, i.e. the kind and type of injection device, by identifying the injection device 16. Various options for identifying the injection device 16 may be implemented depending on available hardware resources of the smartphone:

1. The software may comprise image processing capability, with which a captured image showing the injection device 16 may be processed and in the course of the processing characteristic features of the injection device may be detected such as the form of the entire injection device 16 or the form of parts of the device 16, particularly of the device's housing 160, the form, particularly the length of a needle 161, the form, particularly the dimensions of a drug container 162, and/or the color of the entire device 16 or of parts 160, 161, 162 of the device 16, and/or a code 163, a tag such as a QR-tag, a label printed on the housing 160 or another part such the drug container 162. The code 163, the tag, the label may be detected by OCR (Optical Character Recognition) technology.

2. The software may upload a captured image showing the injection device 16 via a data connection to an image processing service provider such as a web service or an image processing program executed by a computer, which is connected to the smartphone 10. Thus, the software and the smartphone itself do not need to provide image processing capabilities, which sometimes require computing resources beyond the capabilities of smartphones.

3. If the smartphone 10 is equipped with a wireless receiver, for example a Bluetooth® receiver, a NFC (Near Field Communication) reader and/or a RFID (Radio Frequency Identification) reader, and the injection device 16 comprises a Bluetooth® transmitter, a NFC tag and/or a RFID tag, the processor of the smartphone 10 can obtain injection device identification data via a wireless data connection 164 between the smartphone 10 and the injection device 16. The identification data may be stored in an internal memory of the injection device 16 and/or the NFC tag and/or RFID tag. The identification data can also be transmitted via a IR (infrared) or an optical data connection, or by means of a wired data connection for instance comprising an USB (Universal Serial Bus) data connection.

When the injection device 16 is identified by one of the above processes, the software proceeds with obtaining data on the use of the identified injection device 16 (use support data). The use support data can be part of the application or streamed/downloaded from servers, which requires a high-speed internet connection, and may comprise training information on use of the identified injection device such as video, textual, audio, image information, for instance training videos (user steps/step by step training), device usage history or safety information for a user. The use support data may also comprise information on accessories shown in a captured image of the injection device.

The use support data may be received from various sources as listed in the following:

1. The use support data may be stored in an internal storage of the smartphone, for instance can be part of the software, and, thus can be loaded by the processor in the smartphone's main memory for further processing.
2. The use support data may also be stored in an external storage such as a server, a webserver or the like. In such case, the software may configure the processor of the smartphone to contact the external storage via a data connection, for example a wireless data connection, and to download and/or stream the required use support data into the main memory of the smartphone for further processing.
3. The use support data may also be obtained from an internal storage of the injection device such as non-volatile memory of an electronic integrated in the injection device. For instance, the injection device may be equipped with an electronic comprising a controller, a wireless transceiver, and a non-volatile memory. The use support data may be stored in the non-volatile memory. The software executed by the processor of the smartphone may configure the processor to establish a wireless data connection with the wireless transceiver of the injection device's integrated electronic depending on the identified injection device. Upon establishment of the wireless data connection, the software may request the stored use support data and receive the requested data via the established wireless data connection.

After obtaining the use support data for the identified injection device 16, the software proceeds with configuring the processor to generate one or more overlays on the display 12. The overlays may be generated such that they may give a user of the injection device 16 support on its use, particularly by means of boxes 120, 121 containing textual information on the use of certain parts of the injection device 16 and a textual information 122 with the injection device's 16 identification code. The textual information boxes 120, 121 may be displayed near, at or over the respective parts of the captured image of the injection device on the display 12 so that a user can immediately get hints on using the injection device by seeing the textual information boxes 120, 121. But also, a video and/or image(s) may be displayed by one or more overlays. The video and/or image may be for instance displayed in a transparent mode such that it overlays the captured image of the injection device on the display 12 and may demonstrate a proper use of the injection device.

The generation of the one or more overlays on the display 12 comprises an adaptation of the overlays depending on a context of application of the injection device 16 in order to better assist a user or patient in using the injection device.

The adaptation of the overlays may comprise displaying an overlay in different colors, altering the displayed content of the overlay, altering the size of the overlay, selecting the position of the overlay. The context of application of the injection device 16 may comprise one or more environmental conditions such as ambient light, temperature, time and/or date, and one or more injection related conditions such as use history of the injection device, drug, injection site, dosage. Examples of an adaptation of an overlay depending on the context of an application of the injection device are listed in the following:

when the ambient light is below a certain threshold the color and/or size of an overlay may be altered in order to make it easier for a patient to recognize the overlay under bad lighting conditions;

when the temperature is outside a recommended or required range for the injection, the conent of an overlay may be altered to display a warning message, and/or the color of an overlay may be changed to a color such as red or yellow to warn a patient of non-suitable environmental condition for an injection, and/or the size of an overlay may be increased such that a patient cannot overlook it;

when the time and/or date differs from a prescribed medication plan, the content, color, size and/or position of an overlay may be altered such that a patient can easily recognize the overlay and note that an injection is actually not required and prescribed;

when the use history of the injection device shows that actually an injection is (not) necessary and/or (not) prescribed, the content, color, size and/or position of an overlay may be altered such that a patient can easily recognize the overlay and note that an injection is actually (not) required and prescribed, and can also see when the last injection has occurred;

the drug can be displayed by a respectively adapted overlay, for example changing size, position, color, and/or content of the overlay informing a patient of the kind of drug and the drug itself, such as altering a patient of an important insulin injection with a big red overlay positioned in the middle of a display with a content emphasizing the importance;

an injection site can be shown by an overlay with a highlighting color and a position on the display, where the injection site is shown so that a patient is assisted in making the injection;

a dosage to be injected can be shown by selecting an overlay representing the required dosage, for example by showing an icon representing the dosage in a color and/or size which allow a patient to easily recognize the required dosage.

Figure 3:
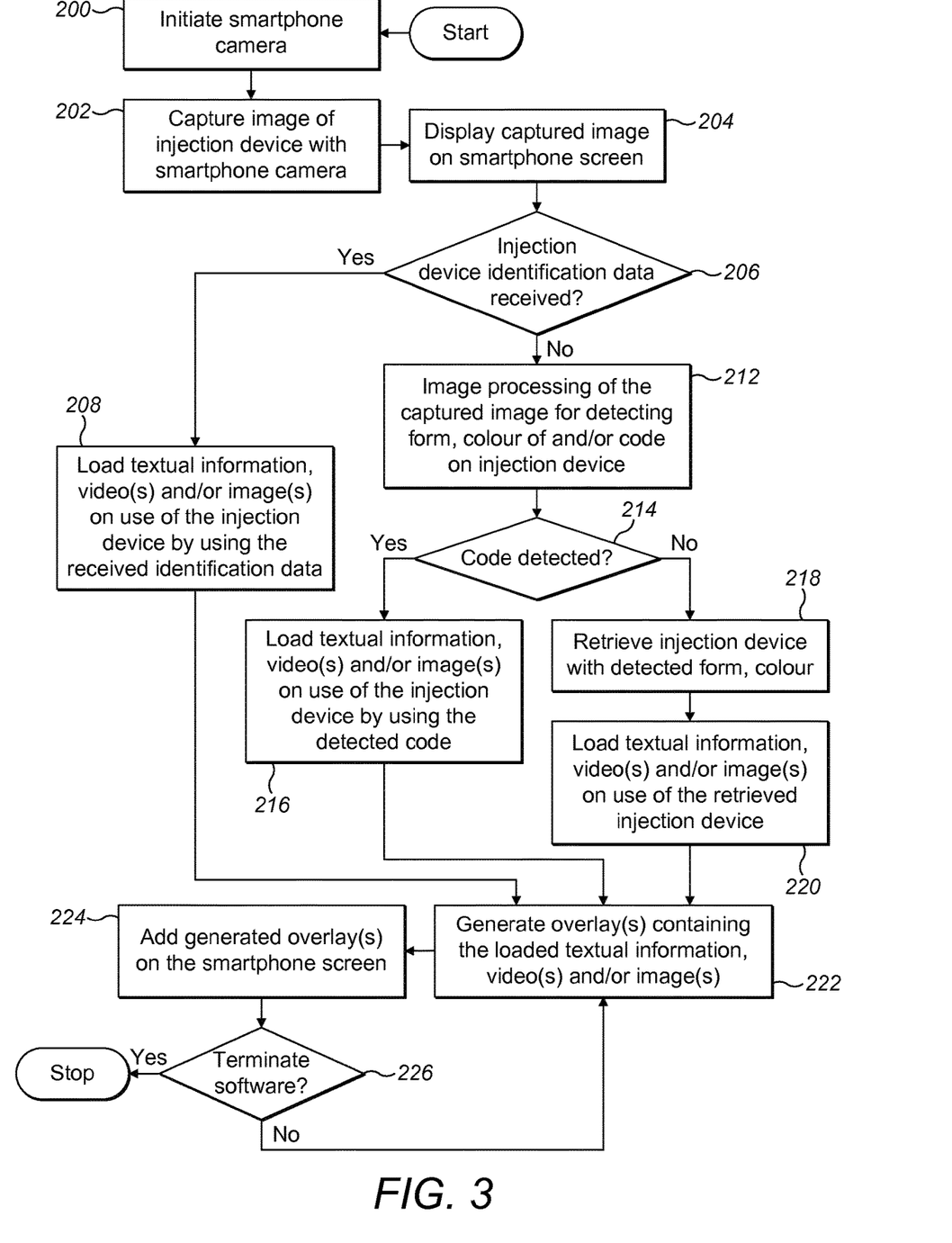
FIG. 3 shows a flowchart of a method according to embodiments.

FIG. 3 shows a flowchart of the software executed by the processor of the smartphone. After launching the software on the smartphone (step START), the software initiates in step 200 the built-in smartphone camera 14 to capture images of the injection device 16 in a subsequent step 202. The captured images are displayed on the smartphone screen in step 204, thus, showing a real representation of the injection device, i.e. the "reality". In step 206, the software checks whether identification data were received from the injection device 16, either wirelessly or wired. If identification data were received, the software continues in step 208 with loading textual information, video(s) and/or image(s) on use of the injection device 16 by using the received identification data from one or more of the sources as explained before. If no identification data were received, the software proceeds with step 212 instead of step 208 and initiates an image processing of a captured image of the injection device 16 for detecting form, color of and/or a code on the injection device. In step 214, the software checks whether a code was detected by the image processing, and if so proceeds with step 216, in which textual information, video(s) and/or image(s) on use of the injection device 16 are loaded by using the detected code from one or more of the sources as explained before. If no code was detected by the image processing, the software retrieves the injection device with the detected form and/or color in step 218, and loads textual information, video(s) and/or image(s) on use of the retrieved injection device 16 in the following step 220. In step 222 following steps 208, 216, and 220, the software then generates one or more overlays containing the loaded information and adds them in subsequent step 224 on the smartphone display or screen to overlay the representation of the "real" injection device 16 to create an augmented reality for the user. In step 226, the software checks whether a termination command was received, and if so stops to execute. Until no termination command is detected in step 226, the software cycles through steps 222 and 224 to generate and add overlay(s) on the smartphone screen, wherein the content of the overlay may vary through each cycle, for instance may display a step by step guidance for the user.

In the following, some further possible applications and implementation of the embodiments are briefly described:

The augmented reality created by the software can be also used to audit and document the use of the injection device 16. A step by step training may for instance visualize the user steps. There may be a subsequent control (via (photo—) camera) for the performed user steps, which means the user imitates the shown visualizations and the software controls the user actions and gives feedback. In case of a correct user step the training continues showing the next step, in case of a wrong user step it gives an alert for instance and the training is not continued until the user is able to perform the respective step correctly. The users get the confirmation that they are using the device correctly. The software may also give alerts if errors or misuse is detected and proposes solutions. The feedback can be visible (text, image or light), audible (sound) or haptic (vibration alert). This shall enhance confidence as well as user understanding.

The smartphone 10 can be put down while using the application without interruption (pauses can be recognized e.g. for performing a two-handed step). Thereby the user can skip information or there may be a procedure which detects the condition of the injection device 16 by means of significant changed geometries on the injector device (e.g. cap attached vs. not attached).

The user can document the injection site, time and dose manually in the software or it can be documented when the camera 14 films it. The application could also give notifications like alerts at defined times when the user should inject the drug. It could also validate if the correct drug is used depending on user information. Alerts can be programmed as reminders e.g. when the injection device should be taken out of the refrigerator or when to inject after a defined acclimatizing temperature has been reached. An electronic, for instance a RFID chip integrated into the injection device 16 could additionally report status of the injection and confirm successful injection; the information could directly be logged in an injection track record.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide. Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten. An examples of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present specification include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. A system for supporting a use of an injection device, the system comprising:
   a display; and
   a processor being configured to determine the injection device, to obtain data on the use of the determined injection device, and to add at least one overlay on the display,
   wherein the at least one overlay is generated depending on the obtained data of the use of the determined injection device,
   wherein the processor is configured to adapt the at least one overlay depending on a context of application of the injection device, the context of application of the injection device comprising at least one of the following: ambient light; time; date, temperature, use history of the injection device, drug, injection site, and dosage, and
   wherein the processor is configured to perform a process for determining the injection device, the process comprising:
      checking whether identification data were received, either wirelessly or wired, from the injection device,
      if identification data were received wirelessly or wired, determining the injection device based on a received identification data, and
      if no identification data were received wirelessly or wired, initiating an image processing of a captured image of the injection device for detecting form, color of and/or a code on the injection device, and determining the injection device based on a detected code, and based on a detected form and/or color if no code was detected by the image processing of the captured image of the injection device.

2. The system of claim 1, wherein the at least one overlay comprises textual information, a video, and/or one or more images.

3. The system of claim 1, wherein the image processing comprises detecting a form of, a color of, a code, a tag and/or a label on the injection device, and determining the injection device depending on the detected form, color, code, tag, and/or label.

4. The system of claim 1, comprising an image capturing component to capture the image of the injection device, wherein the processor is configured to display the captured image of the injection device on the display together with the at least one overlay.

5. The system of claim 1, wherein the processor is configured to generate the at least one overlay by loading the data on the use of the determined injection device from an internal storage and/or from an external storage by a data connection.

6. The system of claim 1, wherein the processor is configured to detect a user action and to adapt the overlay depending on the detected user action.

7. The system of claim 1, wherein the processor is configured to store data regarding a use history of the injection device.

8. The system of claim 1, wherein adapting of the at least one overlay depending on a context of application of the injection device comprises displaying the overlay in different colors depending on at least one of the following: ambient light; time; date, temperature, use history of the injection device, drug, injection site, and dosage.

9. The system of claim 1, wherein adapting of the at least one overlay depending on a context of application of the injection device comprises altering displayed content of the overlay depending on at least one of the following: ambient light, time, date, temperature, use history of the injection device, drug, injection site, and dosage.

10. The system of claim 1, wherein adapting of the at least one overlay depending on a context of application of the injection device comprises altering a size of the overlay depending on at least one of the following: ambient light, time, date, temperature, use history of the injection device, drug, injection site, and dosage.

11. The system of claim 1, wherein adapting of the at least one overlay depending on a context of application of the injection device comprises selecting a position of the overlay on the display depending on at least one of the following: ambient light, time, date, temperature, use history of the injection device, drug, injection site, and dosage.

12. The system of claim 1, wherein the processor is configured to determine the injection device based on the image processing of the captured image of the injection device when the identification data has not been received by
   determining whether a code has been detected based on the image processing,
   determining the injection device based on the detected code when the code has been detected, and determining the injection device based on the detected form and/or color of the injection device when the code has not been detected.

13. A method comprising
determining an injection device,
obtaining data on a use of the determined injection device, and
adding at least one overlay on a display,
wherein the at least one overlay is generated depending on the obtained data of the use of the determined injection device, and adapted depending on a context of application of the injection device, the context of application of the injection device comprising at least one of the following: ambient light, time, date, temperature, use history of the injection device, drug, injection site, and dosage, and
wherein the determining of the injection device comprises:
  checking whether identification data were received, either wirelessly or wired, from the injection device;
  if identification data were received wirelessly or wired, determining the injection device based on a received identification data; and
  if no identification data were received wirelessly or wired, initiating an image processing of a captured image of the injection device for detecting form, color of and/or a code on the injection device and determining the injection device based on a detected code, and based on a detected form and/or color if no code was detected by the image processing of the captured image of the injection device.

14. The method of claim 13, wherein the at least one overlay comprises textual information, a video, and/or one or more images.

15. The method of claim 13, wherein the image processing comprises detecting a form of, a color of, a code, a tag and/or a label on the injection device, and determining the injection device depending on the detected form, color, code, tag, and/or label.

16. The method of claim 13, wherein determining the injection device based on the image processing of the captured image of the injection device when the identification data has not been received comprises
  determining whether a code has been detected based on the image processing,
  determining the injection device based on the detected code when the code has been detected, and
  determining the injection device based on the detected form and/or color of the injection device when the code has not been detected.

17. A device comprising:
a processor,
a memory,
a display,
a camera, and
software stored in a non-volatile part of the memory,
wherein the software configures the processor of the device to capture one or more images of an injection device with the camera, to show a captured image of the injection device on the display, to determine the injection device, to obtain data on use of the determined injection device and to add at least one overlay on the display,
wherein the at least one overlay is generated depending on the obtained data on use of the determined injection device and adapted depending on a context of application of the injection device, the context of application of the injection device comprising at least one of the following: ambient light, time, date, temperature, use history of the injection device, drug, injection site, and dosage, and
wherein the determining of the injection device comprises:
  checking whether identification data were received, either wirelessly or wired, from the injection device,
  if identification data were received wirelessly or wired, determining the injection device based on a received identification data, and
  if no identification data were received wirelessly or wired, initiating an image processing of a captured image of the injection device for detecting a form, a color of and/or a code on the injection device and determining the injection device based on a detected code, and based on a detected form and/or color if no code was detected by the image processing of the captured image of the injection device.

18. The device of claim 17, wherein the device is a smartphone, a Personal Digital Assistant, a tablet or laptop computer, or a head-mounted display device.

19. The device of claim 17, wherein the at least one overlay comprises textual information, a video, and/or one or more images.

20. The device of claim 17, wherein the image processing comprises detecting a form of, a color of, a code, a tag and/or a label on the injection device, and determining the injection device depending on a detected form, color, code, tag and/or a detected label.

* * * * *

UNITED STATES PATENT AND TRADEMARK OFFICE
CERTIFICATE OF CORRECTION

| | |
|---|---|
| PATENT NO. | : 11,631,487 B2 |
| APPLICATION NO. | : 16/763289 |
| DATED | : April 18, 2023 |
| INVENTOR(S) | : Stefan Wendland, Michael Harms and Zdenek Cerman |

It is certified that error appears in the above-identified patent and that said Letters Patent is hereby corrected as shown below:

In the Claims

In Column 11, Line 60, Claim 1, delete "time;" and insert -- time, --

In Column 12, Line 40, Claim 8, delete "ambient light; time;" and insert -- ambient light, time, --

Signed and Sealed this
Twelfth Day of September, 2023

*Katherine Kelly Vidal*

Katherine Kelly Vidal
*Director of the United States Patent and Trademark Office*